United States Patent
Ishikawa

(10) Patent No.: US 9,155,909 B2
(45) Date of Patent: Oct. 13, 2015

(54) RADIATION THERAPY APPARATUS

(75) Inventor: Masayori Ishikawa, Sapporo (JP)

(73) Assignee: NATIONAL UNIVERSITY CORPORATION HOKKAIDO UNIVERSITY (JP)

( * ) Notice: Subject to any disclaimer, the term of this patent is extended or adjusted under 35 U.S.C. 154(b) by 851 days.

(21) Appl. No.: 13/257,817

(22) PCT Filed: Mar. 23, 2010

(86) PCT No.: PCT/JP2010/054958
§ 371 (c)(1),
(2), (4) Date: Sep. 20, 2011

(87) PCT Pub. No.: WO2010/110255
PCT Pub. Date: Sep. 30, 2010

(65) Prior Publication Data
US 2012/0006990 A1   Jan. 12, 2012

(30) Foreign Application Priority Data
Mar. 24, 2009   (JP) ................................ 2009-072665

(51) Int. Cl.
*G01T 1/00*     (2006.01)
*G01N 23/04*   (2006.01)
(Continued)

(52) U.S. Cl.
CPC ............ *A61N 5/1049* (2013.01); *A61N 5/1037* (2013.01); *A61N 5/1039* (2013.01);
(Continued)

(58) Field of Classification Search
CPC .. A61N 5/1037; A61B 6/4429; G01T 1/2914; G01T 1/2921

USPC ............ 250/263.03, 354.1, 393; 607/88, 901; 378/26, 901, 63, 65
See application file for complete search history.

(56) References Cited

U.S. PATENT DOCUMENTS

2004/0081269 A1*  4/2004  Pan et al. ...................... 378/4
2006/0086905 A1*  4/2006  Fritzler et al. ........... 250/363.05
(Continued)

FOREIGN PATENT DOCUMENTS

EP    2127697 A1   12/2009
JP    64-27569 A    1/1989
(Continued)

OTHER PUBLICATIONS

Detection of Lung Tumor Movement in Real-Time tumor-Tracking Radiotherapy, International Journal of Radiation: Oncology Biology Physics, vol. 51, Jan. 2001, pp. 304-310.*
(Continued)

*Primary Examiner* — David Porta
*Assistant Examiner* — Carolyn Igyarto
(74) *Attorney, Agent, or Firm* — Cantor Colburn LLP

(57) ABSTRACT

An organism is irradiated with therapeutic radiation from a radiation irradiation device. A pair of two-dimensional radiation detectors are arranged so as to face one another with the irradiated therapeutic radiation passing therebetween, and detect the two-dimensional positions irradiated by a pair of annihilation γ rays produced when a positron emitted from a positron-emitting radionuclide is annihilated. On the basis of a pair of positions detected by the pair of two-dimensional radiation detectors, a radionuclide position detecting unit detects the position of the positron-emitting radionuclide, and the radiation irradiation device irradiates the position of the positron-emitting radionuclide with therapeutic radiation.

3 Claims, 5 Drawing Sheets
(1 of 5 Drawing Sheet(s) Filed in Color)

(51) Int. Cl.
*A61N 5/10* (2006.01)
*G06T 7/00* (2006.01)
*A61B 6/00* (2006.01)
*A61N 5/06* (2006.01)

(52) U.S. Cl.
CPC .............. *A61N5/1067* (2013.01); *G06T 7/004* (2013.01); *A61B 6/52* (2013.01); *A61N 5/1065* (2013.01); *A61N 2005/0626* (2013.01); *A61N 2005/1052* (2013.01)

(56) References Cited

U.S. PATENT DOCUMENTS

| 2008/0135764 | A1 | 6/2008 | Braess |
| 2010/0038547 | A1 | 2/2010 | Ishikawa |
| 2010/0054412 | A1 | 3/2010 | Brinks et al. |
| 2010/0142677 | A1 | 6/2010 | Kaneko et al. |

FOREIGN PATENT DOCUMENTS

| JP | 2008-173299 A | 7/2008 |
| WO | 2008/038662 A1 | 4/2008 |
| WO | 2008/102843 A1 | 8/2008 |
| WO | 2008096285 A2 | 8/2008 |

OTHER PUBLICATIONS

Dirk Verellen et al., "Innovations in image-guided radiotherapy", Nature Reviews Cancer, vol. 7, No. 12, Dec. 2007, pp. 949-960.
The extended European search report for European patent application No. 10756051.8 mailing date of Aug. 28, 2012.
International Search Report for International Application No. PCT/JP2010/054958 mailed Apr. 20, 2010 with English translation.

* cited by examiner

RADIATION THERAPY APPARATUS

This is a U.S. national stage of application No. PCT/JP2010/054958, filed on Mar. 23, 2010. Priority under 35 U.S.C. §119(a) and 35 U.S.C. §365(b) is claimed from Japanese Application No. 2009-072665, filed Mar. 24, 2009, the disclosure of which is also incorporated herein by reference.

TECHNICAL FIELD

The present invention relates to a radiation therapy apparatus which irradiates an organism to perform therapy with respect to the organism.

BACKGROUND ART

In recent years, tumor localization by means of molecular imaging such as positron emission tomography (PET) or the like is being performed in radiation therapy. Specifically, PET imaging is performed before starting the radiation therapy, and tomographic images thus obtained are used for developing a treatment plan. It is, however, difficult for PET imaging to track the movement of a tumor in real time.

In real-time tumor tracking radiation therapy apparatuses capable of tracking the movement of a tumor in real time, on the other hand, a metal marker inserted in the patient body near the tumor is detected by a pair of X-ray fluoroscopic apparatuses and the three-dimensional position of the metal marker is calculated for controlling irradiation based on the obtained position of the metal marker.

PRIOR ART REFERENCE

Patent Literature

Patent Literature 1: WO2008/038662A1

SUMMARY OF THE INVENTION

Problems to be Solved by the Invention

However, the above-described real-time tumor tracking radiation therapy apparatuses suffer from the problems that invasive manipulation is necessary when introducing the metal marker and that tracking of a tumor itself is difficult.

Means for Solving the Problems

In accordance with an aspect of the invention, there is provided a radiation therapy apparatus for treating an organism with irradiating therapeutic radiation on the organism, the radiation therapy apparatus including a pair of two-dimensional radiation detectors which are arranged so as to be opposed to each other with the therapeutic radiation which is emitted passing therebetween and which detect an incident two-dimensional positions of a pair of annihilation γ rays produced when positrons emitted from a positron-emitting radionuclide annihilate, a radionuclide position detecting unit which detects a position of the positron-emitting radionuclide in accordance with a pair of positions detected by the pair of two-dimensional radiation detectors, and a radiation irradiation device which irradiates the therapeutic radiation toward the position of the positron-emitting radionuclide.

Further, it is preferable that the radionuclide position detecting unit detects the position of the positron-emitting radionuclide only with respect to positions of the radionuclide whose moving distance or moving rate is a predetermined value or less, among positions detected in time series.

Also, it is preferable that the radionuclide position detecting unit determines the position of the positron-emitting radionuclide in a direction connecting the pair of two-dimensional radiation detectors, in accordance with an irradiation position of the therapeutic radiation from the radiation irradiation device.

In addition, it is preferable that the radionuclide position detecting unit assumes that, in a time range in which it is estimated that each portion in the organism is located at substantially the same position, the positron-emitting radionuclide exists at a point where a line connecting the pair of two-dimensional radiation detectors determined by simultaneous detection intersects a plane of interest located between the pair of detectors, and determines whether or not the positron-emitting radionuclide is on the plane of interest by determining whether or not a distribution formed by positions of the positron-emitting radionuclide detected in time series is within a predetermined range on the plane of interest.

It is also preferable that, in the radionuclide position detecting unit, when the position of the detected positron-emitting radionuclide is within an irradiation range of radiation emitted by the radiation irradiation device, the radiation irradiation device performs irradiation of the therapeutic radiation.

Advantages of the Invention

According to the present invention, by accumulating positron-emitting radionuclide such as FDG in a tumor which is moving due to breathing or the like, and detecting two annihilation γ rays produced when positrons annihilate, the position of the positron-emitting radionuclide can be calculated in real time. It is therefore possible to irradiate the tumor with radiation in a reliable manner in synchronization with the detected tumor position.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
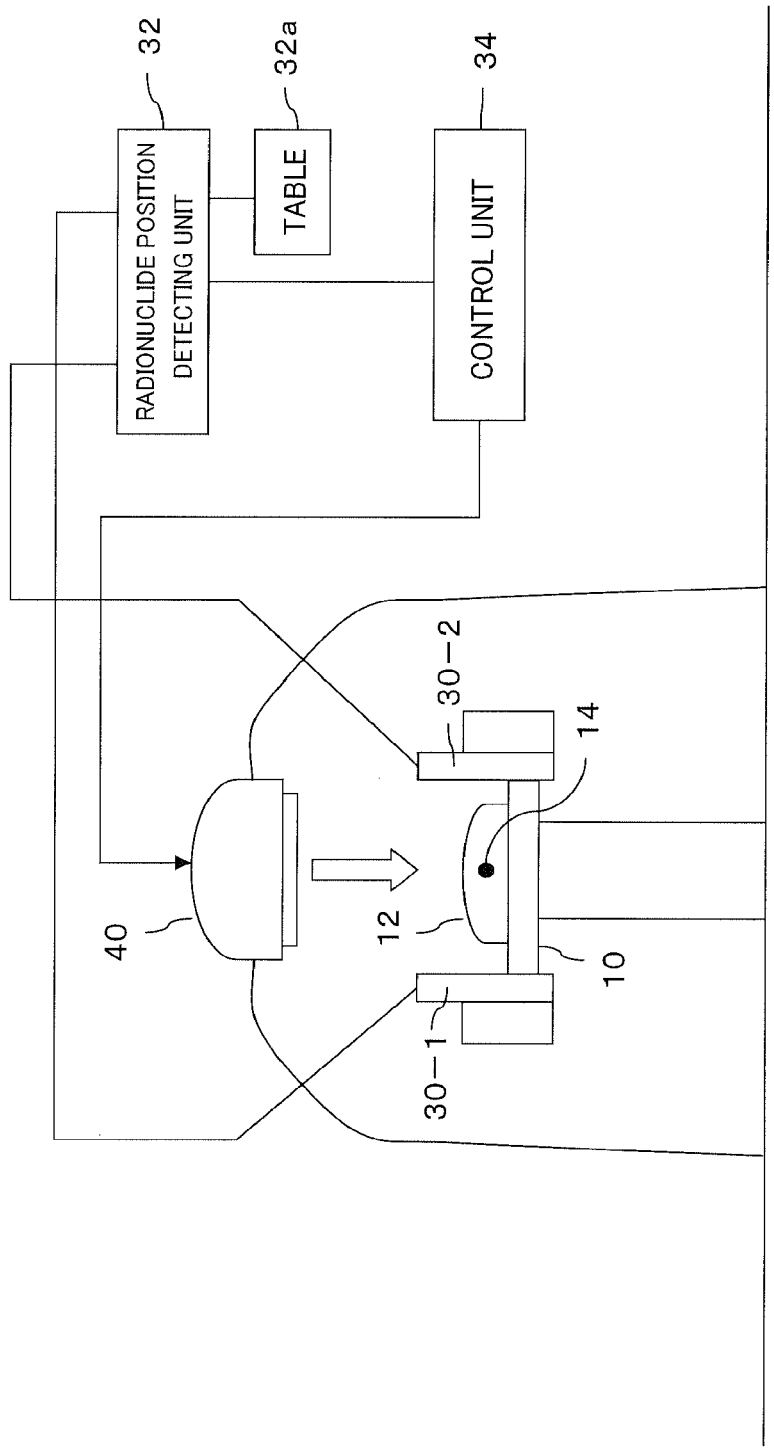
FIG. 1 View illustrating an overall structure of a radiation therapy apparatus according to an embodiment of the present invention.

An embodiment of a radiation therapy apparatus according to the present invention will be described with reference to the drawings. FIG. 1 is a view illustrating the overall structure of a radiation therapy apparatus.

There exists a tumor 14 within a body of a patient 12 fixed on a therapy table 10. According to the present embodiment, as in PET test, positron-emitting radionuclide such as FDG ($^{18}$F-FDG: $^{18}$F-fluorodeoxy glucose) is previously administered into the patient 12. The positron-emitting radionuclide decays in the body, thereby releasing a single positron. The emitted positron binds to an electron of atoms (normally water) in the vicinity and is then annihilated with releasing two γ (gamma) rays having an energy which is equal to the rest mass of the electron. These γ rays, retaining the momentums of the original electron and positron, have completely opposite momentums and are therefore released in a pair in directions which are different from each other by 180 degrees (i.e. opposite directions).

Here, FDG will accumulate in a cancer tissue (tumor) in which glucose metabolism is active. Accordingly, in a tumor, a pair of annihilation γ rays are sequentially emitted in the opposite directions.

Figure 2:
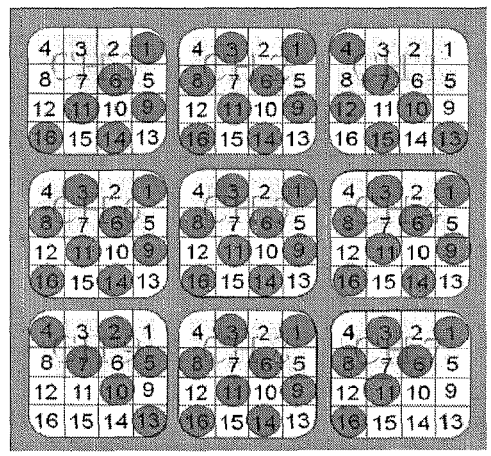
FIG. 2 View illustrating a structure of a two-dimensional radiation detecting device.

On both sides of the patient 12, two-dimensional radiation detectors 30-1 and 30-2 are placed in parallel to each other for detecting the positions of γ-ray emittion. This two-dimensional radiation detector 30 is composed of a number of γ-ray detectors arranged in a plane. FIG. 2 shows an example of the detector that is composed of the arranged nine units each formed of 16 γ-ray detectors. While, in the present embodiment, only 64 γ-ray detectors indicated by black circles are used, the detection accuracy can be increased by using a greater number of γ-ray detectors which are smaller in size.

The outputs from the two-dimensional radiation detectors 30-1 and 30-2 are supplied to a radionuclide position detecting unit 32. Signals from the respective γ-ray detectors are independently supplied to the radionuclide position detecting unit 32. When the γ rays are detected simultaneously by the two two-dimensional radiation detectors 30-1 and 30-2, the radionuclide position detecting unit 32 specifies the position of the positron-emitting radionuclide, based on the detected positions of the two γ rays. In this example, table 32a which specifies the position of the positron-emitting radionuclide when simultaneous counting is performed in each pair of the g-ray detectors in the two-dimensional radiation detectors 30-1 and 30-2 is provided, and the position of the positron-emitting radionuclide is specified with reference to this table 32a.

Figure 3:
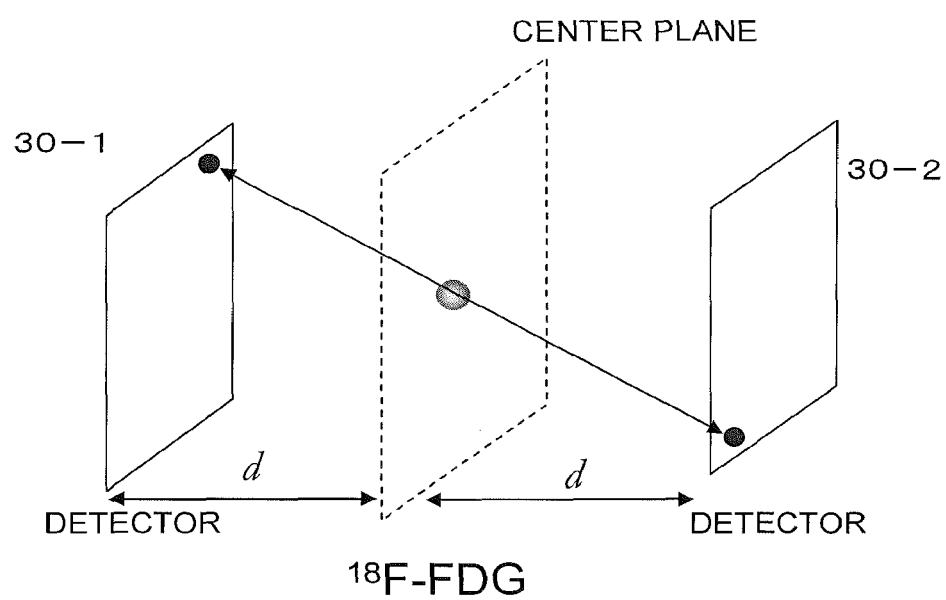
FIG. 3 View illustrating the detection of position when a target is located on a center plane.

Specifically, as illustrated in FIG. 3, when two specific γ-ray detectors of the two-dimensional radiation detectors 30-1 and 30-2 detect γ rays simultaneously, it can be determined that the positron-emitting radionuclide exists on the line connecting these two γ-ray detectors. Further, in the present embodiment, by assuming that the positron-emitting radionuclide is located in the middle between the two two-dimensional radiation detectors 30-1 and 30-2, the position of the positron-emitting radionuclide obtained when the two γ-ray detectors perform simultaneous counting is specified. These correspondences are previously registered in table 32a. It is therefore possible to detect the position of the positron-emitting radionuclide immediately when such simultaneous counting is performed.

In the apparatus according to the present embodiment, as the temporal resolution in the radionuclide position detecting unit 32 is approximately 100 nsec, it is possible to perform sufficient tracking with respect to the movement of a tumor due to breathing or the like (1 to several tens of mm/s). Further, according to the technology of the present embodiment, the temporal resolution can be increased to the order of nsec.

The output of the radionuclide position detecting unit 32 is supplied to a control unit 34, which controls the radiation irradiation apparatus 40. More specifically, the control unit 34 controls the radiation irradiation apparatus 40 such that the radiation irradiation apparatus 40 emits therapeutic radiation only when the detected radionuclide position is located within the irradiation range of the therapeutic radiation from the radiation irradiation apparatus 40. With this control, it is possible to reliably irradiate the tumor with the therapeutic radiation.

The position detection in the radionuclide position detecting unit 32 will be further described in detail. The vessel containing 450 kBg of FDG was placed in the center between the two-dimensional radiation detectors 30-1 and 30-2 and was caused to move at 10 mm/s and 50 mm/s in a reciprocating manner in parallel to the two-dimensional radiation detectors 30-1 and 30-2, and the position detection was performed.

Figure 4:
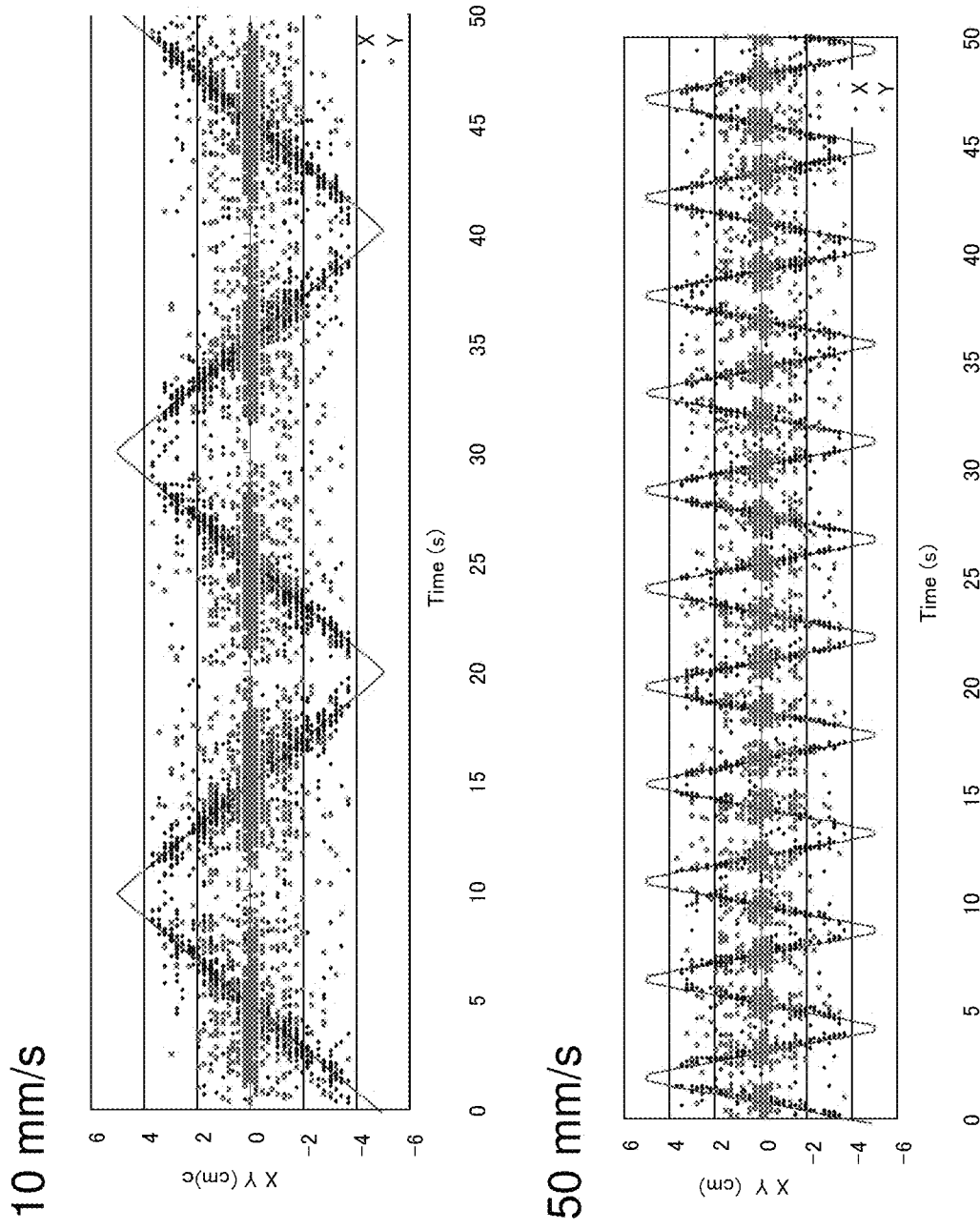
FIG. 4 View illustrating position data before processing.

FIG. 4 illustrates data concerning the positions obtained by the radionuclide position detecting unit 32, which is original data without any processing. In the drawings, dark-color circles represent data concerning the moving direction (X direction) of a target, and light-color circles represent data concerning the height direction (Y direction) orthogonal to the moving direction. The actual target positions in the X direction are along the line in the triangular wave shape indicated by a solid black line. On the other hand, as positions in the Y direction do not basically move, the actual target positions in the Y direction are on the zero line. As can be clearly seen in the drawings, the measured positions significantly vary in the original data.

Figure 5:
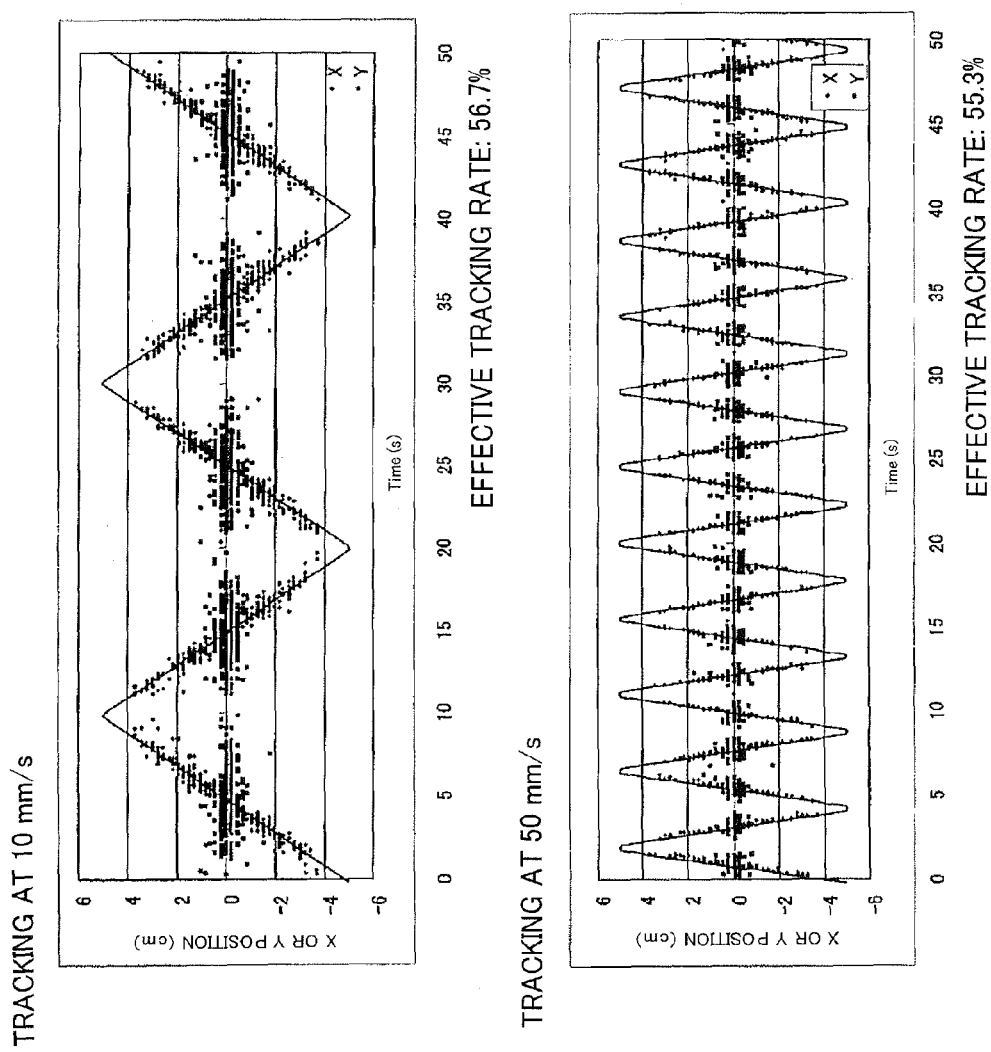
FIG. 5 View illustrating position data after processing.

Thus, a threshold value (T mm) is set concerning the movement of the detected positions in two detection events. Specifically, only positions whose moving distance is within T mm in two detection events (in the preceding and following tracking events) are adopted, whereas detected positions whose moving distance exceeds that range are excluded. FIG. 5 illustrates an example in which T=10 mm is set. As illustrated, it can be understood that the detection accuracy can be improved by setting the threshold value T. Assuming that the tolerance of a difference between a detected position and the actual position is 5 mm, the ratio that satisfy the tolerance was 57.8% at the moving rate of 10 mm/s and was 51.6% at the moving rate of 50 mm/s in the original data, whereas the ratio was 78.9% at the moving rate of 10 mm/s and was 70.6% at the moving rate of 50 mm/s when processing by means of the threshold value was performed. Further, when these results were evaluated by using the average distance of the measured values error (mean error), the mean error was 8.69 mm at the moving rate of 10 mm/s and 9.06 mm at the moving rate of 50 mm/s in the original data, whereas the mean error was 1.87 mm at the moving rate of 10 mm/s and 1.78 mm at the moving rate of 50 mm/s when processing by means of the threshold value was performed. This indicates that the position of FDG can be tracked with sufficient accuracy by the setting of the threshold value.

The above-described threshold value may be determined in accordance with the moving rate of the target. Here, while the threshold value described above is a distance, it is preferable that the moving rate obtained by dividing the moving distance in two detection events by a time interval between these two detection events is used as the threshold value. For example, it is desirable to set the moving rate, which is the threshold value, to a value around the upper limit value of the moving rate of the target. It is also possible to set the threshold value to a value around the average rate. Excluding data with large movement which actually occurred would not cause significant problems as it only make irradiation of therapeutic radiation difficult to perform concerning such data. As such, the threshold value of the moving rate is determined in accordance with the moving rate of the target.

Here, according to the present embodiment, in the direction connecting the two two-dimensional radiation detectors 30-1 and 30-2 position detection of the target (tumor containing a positron-emitting radionuclide) is performed with fixation to the center plane between the two-dimensional radiation detectors 30-1 and 30-2. In other words, this center plane serves as a plane of interest located between the line determined by simultaneous detection that connects the pair of two-dimensional radiation detectors and the pair of detectors. This is because the therapeutic radiation is emitted only when the target is located at a predetermined position within the center plane.

Figure 6:
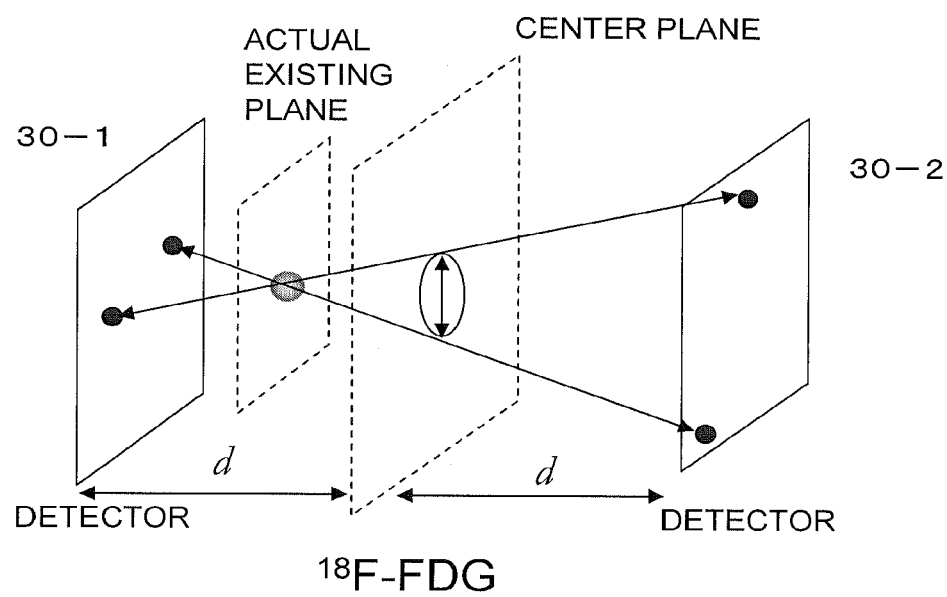
FIG. 6 View illustrating the detection of position when a target is not located on a center plane.

When the target is not located on the center plane, the target position is not correct. More specifically, in this case, as illustrated in FIG. 6, while the target has a given size on the actual target existing plane, the target position on the center plane is distributed in a larger range. Accordingly, in such a case, the target position cannot be specified.

In the present embodiment, when the detected target position on the center plane within a predetermined time period is not in a predetermined range, it is determined that the target does not exist on the center plane and irradiation of therapeutic radiation is not performed. Accordingly, it is possible to emit the therapeutic radiation to the target only when the target is located within the irradiation range of the therapeutic radiation.

For example, when the distribution of the position detected in 0.01 seconds is twice the normal size of the target or smaller, it can be determined that the target is on the center plane. Further, it is also possible to determine that the target is on the center plane when the distribution (e.g. standard deviation) of the position detected within a predetermined time period is a predetermined value ($\sigma=5$ mm) or less.

As described above, according to the present embodiment, only targets existing on the center plane can be tracked because the resolution is significantly lowered (i.e. an image is not formed) when the target (tumor in which a positron-emitting radionuclide exists) is not on the center plane disposed between the two-dimensional radiation detectors 30-1 and 30-2. Further, according to the present embodiment, as computation processing in nsec is possible, the apparatus can be applied to a tumor having a size of 1 cm or less which is suitable for radiation therapy. Here, it has been reported that, concerning lung cancer for which movement of a target is most relevant, the movement of the target in the front-back direction is 1 to 12 mm on average (1 to 20 mm), whereas the movement of the target in the right-left direction is 1 mm on average (0 to 1 mm). According to the present embodiment, sufficient tracking is possible in the front-back direction, and further, in the right-left direction, the target can be detected by detecting no image formation, so that irradiation of therapeutic radiation in this case can be avoided.

While the radiation irradiation device 40 of the present embodiment has been described as a device for emitting the therapeutic radiation in a fixed direction, the radiation irradiation device 40 may emit the therapeutic radiation while rotating. By emitting the therapeutic radiation while rotating, the radiation irradiation device 40 is capable of performing rotation intensity modulated radiation therapy or the like.

As described above, according to the present embodiment, the position of the positron-emitting radionuclide is detected in real time by the two-dimensional radiation detectors 30-1 and 30-2, so that irradiation of the therapeutic radiation from the radiation irradiation device 40 can be controlled. This enables tracking a tumor which moves significantly and emit a therapeutic radiation beam to the tumor, thereby suppressing useless irradiation of radiation.

According to the present embodiment, as a medicine such as FDG which is used in molecule imaging can be utilized, it is possible to track a small tumor detected in the PET diagnosis. In particular, as, in the case of a small tumor in early stage cancer, there is often a risk of an invasive procedure for implanting a gold marker, the technology of allowing tracking with low invasiveness would provide great advantages.

Further, accordingly to the present embodiment, because not only tracking of a tumor itself as a target but also identification of position of the tumor is possible without the need for reconstruction of a device required for PET devices, the technology of the present embodiment is also effective as a simple method of identifying the position of a tumor.

REFERENCE NUMERALS

10 therapy table, 12 patient, 14 tumor, 30 two-dimensional radiation detector, 32 radionuclide position detecting unit, 32a table, 34 control unit, 40 radiation irradiation device.

The invention claimed is:

1. A radiation therapy apparatus for treating an organism with irradiating therapeutic radiation on the organism, and for use with a positron-emitting radionuclide, the radiation therapy apparatus comprising:
    a pair of two-dimensional radiation detectors which are arranged so as to be opposed to each other with the therapeutic radiation which is emitted passing therebetween, and detect respectively an incident two-dimensional positions of a pair of annihilation γ rays produced when positrons emitted from the positron-emitting radionuclide annihilate;
    a radionuclide position detecting unit structured to detect a position of the positron-emitting radionuclide on a line connecting a pair of positions detected by the pair of two-dimensional radiation detectors; and
    a radiation irradiation device structured to irradiate the therapeutic radiation toward the position of the positron-emitting radionuclide on a plane of interest;
    wherein radionuclide position detecting unit is structured to assume that the positron-emitting radionuclide exists at a point where the line intersects the plane of interest, which is determined in accordance with the irradiation position of the therapeutic radiation, to determine a provisional position of the positron-emitting radionuclide;
    wherein the radionuclide position detecting unit is structured to determine that the positron-emitting nuclide exists on the plane of interest when a position distribution formed by the determined provisional position of the positron-emitting radionuclide in time series is within a predetermined range on the plane of interest.

2. The radiation therapy apparatus according to claim 1, wherein
    the radionuclide position detecting unit is structured to detect the position of positron-emitting radionuclide only with respect to positions of the positron-emitting radionuclide whose moving distance or moving rate is a predetermined value or less, among positions detected in time series.

3. The radiation therapy apparatus according to claim 1, wherein a controller is structured to allow irradiation of the therapeutic radiation to be performed when, in the radionuclide position detecting unit, the position of the detected positron-emitting radionuclide is within an irradiation range of radiation emitted by the radiation irradiation device, and to prohibit the irradiation of the therapeutic radiation when the position of the detected positron-emitting radionuclide is outside the irradiation range of radiation emitted by the radiation irradiation device.

* * * * *